United States Patent [19]
Camilli et al.

[11] Patent Number: 5,674,702
[45] Date of Patent: Oct. 7, 1997

[54] DETERMINATION OF THE TOXICITY OF WATER USING AN ANAEROBIC BACTERIAL CULTURE

[75] Inventors: Marcello Camilli, Grottaferrata; Umberto Barberini; Andrea Robertiello, both of Rome, all of Italy

[73] Assignee: Eniricerche S.p.A., Milan, Italy

[21] Appl. No.: 379,285

[22] Filed: Jan. 27, 1995

[30] Foreign Application Priority Data

Jan. 28, 1994 [IT] Italy ................. MI94A0141

[51] Int. Cl.$^6$ ................. C12Q 1/18; C12Q 1/20
[52] U.S. Cl. ................. 435/32; 435/33; 435/287.5
[58] Field of Search ................. 435/29, 31, 34, 435/32, 39, 33, 40, 287.1, 287.5, 300.1, 245

[56] References Cited

U.S. PATENT DOCUMENTS

| | | | |
|---|---|---|---|
| 3,907,646 | 9/1975 | Wilkins et al. | 435/287.5 |
| 4,314,029 | 2/1982 | Ohtake et al. | 435/287.5 |
| 4,513,280 | 4/1985 | Hannan et al. | 435/32 |
| 5,142,969 | 9/1992 | Chun | 435/300.1 |
| 5,175,091 | 12/1992 | Hannan | 435/287.5 |
| 5,264,349 | 11/1993 | De Baere | 435/167 |

FOREIGN PATENT DOCUMENTS

| | | | |
|---|---|---|---|
| 330687 | 7/1976 | Australia. | |
| 0200226 | 5/1986 | European Pat. Off.. | |
| 0289976 | 9/1988 | European Pat. Off.. | |
| 486443 | 5/1992 | European Pat. Off. | 435/32 |
| 2063239 | 6/1981 | United Kingdom. | |
| 2087863 | 6/1982 | United Kingdom. | |
| 9201064 | 1/1992 | WIPO. | |

*Primary Examiner*—William H. Beisner
*Attorney, Agent, or Firm*—Oblon, Spivak, McClelland, Maier & Neustadt, P.C.

[57] ABSTRACT

Procedure and relative equipment for determining the presence of toxic substances in water destined for drinking and/or in water effluents, based on the inhibition of the production of biogas (methane) on the part of anaerobic bacterial aggregates.

4 Claims, 3 Drawing Sheets

DETERMINATION OF THE TOXICITY OF WATER USING AN ANAEROBIC BACTERIAL CULTURE

BACKGROUND OF THE INVENTION

1. Field of the Invention

The present invention relates to a biological procedure, which involves the use of anaerobic bacteria, for measuring the toxicity caused by polluting substances in water or water effluents.

2. Detailed of the Related Art

Bacteria are known as being efficient detectors of chemical toxicity as they quickly react to changes in their environment. It is for this reason that many biological tests have been developed for monitoring and controlling toxic substances in water or effluents. In these tests the inhibition of the metabolism of a species of bacteria in the presence of toxic substances is compared with the metabolism of the same species cultivated on a standard substrate.

Different bacterial species are used and various parameters are measured (with respect to this see Toxicity Testing Using Microorganisms vol 1 and 2, B. J. Dutka and G. Bitton publishers, CRC Press 1989). As an example, the bioluminescence of some microorganisms, the motility inversion of *Spirillum volutans*, the measurement of oxygen consumed and ATP produced, etc., can be mentioned.

Tests which use single bacterial species are more sensitive, with the same toxicity of molecule, than those which involve mixed flora, operating in a metabolic chain, such as for example aerobic and anaerobic mud.

This greater sensitivity is made evident by a lesser concentration of a certain toxic substance required for reducing by 50% the standard measurement of the biochemical-biological parameter which is a specific tracer of the method (EC 50, from "effective concentration involving 50% reduction).

Tests carried out with mixed flora distinguished by subsequent metabolic stages can evaluate the toxicity of a substance on different levels. Normally, owing to the syntrophy ratio among microbic populations, the EC 50 of a toxic substance is determined on the final metabolite (for example on methane in the case of anaerobic bacterial aggregates). The production of methane is in fact, in any case reduced, either directly or indirectly by the inhibition of the precursors, by the presence of toxic substances.

Methods which use microbic aggregates, although having lesser sensitivity in an absolute sense, are particularly versatile for testing the total toxicity such as that produced by several compounds contemporaneously present as is observed for example in industrial waste. Tests using a methanogen bacterial biomass were mainly used for the prevention of biodegradability of effluents or mud containing toxic substances. Subsequently tests were developed which were specifically designed for the degree of methanogenic activity of the single trophic groups of the methanobacterial aggregate. The main objectives however concerned the microbiological analysis of the quality and conservability of the inocula to be used in the activation of anaerobic reactors. At the same time, elaborations of the technique perfected the ATA procedures (tests of anaerobic toxicity) in order to check the incidence of toxic substances present in waste on the anaerobic conversion into methane of specific substrates on the part of different kinds of methanobacteria. This kind of procedure involves a series of anaerobic centres (normally microreactors) wherein known quantities, both of anaerobic mud and specific substrate, are reacted in the presence of and without supposedly toxic substances. The possibly different results, produced under the same operating conditions after one or more verifications, is assumed to be the variation index of the gas generating activity of the single trophic-bacterial groups.

All these techniques and their various developments and applications are mainly carried out in research laboratory, in that they cannot be effected other than by the gas-chromatographic analysis of the head spaces of the microreactors. In the case of attempts to obtain analytic systems using pressure transducers on the head of the reactors, complex mechanical-type devices had to be used for connection with the data collecting units.

SUMMARY OF THE INVENTION

A method has now been found, in accordance with the present invention, which involves the use of mixed methanogenic aggregates suitably precultivated, that are useful for evaluating the toxicity produced by a single substance or a wide range of substances in water or water effluents.

In accordance with this, the present invention relates to a biological procedure to determine the toxicity of water and water waste, embodied as follows:

preparation of a mixed methanogenic anaerobic bacterial culture;

inoculation of the bacterial culture into a variety of reactors of which at least one is a reference reactor, containing a substrate with standard water and at least another, a measuring reactor, containing a substrate with water or waste the toxicity of which is to be measured;

said measuring and reference reactors being connected to a detecting system capable of measuring the volume of biogas produced per unit of time;

said detecting system being operatively connected to a data processing system capable of determining the decrease in the production kinetics of the biogas generated by the anaerobic metabolism on the substrate and capable of correlating it with the toxicity of the water or waste.

DESCRIPTION OF THE PREFERRED EMBODIMENTS

The mixed bacterial culture is a methanogen anaerobic aggregate similar to those used for the purification of urban wastes in UASB-type reactors, suitably conditioned to enhance the requisites of its sensitivity to toxic substances.

This greater sensitivity is present in the biomasses with intense cellular reproduction and, in the case of mixed complexes, mainly in the methanobacteria. In fact other populations which catalyze transformations before the reduction of the methyl group have proved to be less sensitive. In addition the sensitivity of a microbic biomass to toxic substances is due, not only to the average age of the complex as a whole, but also to the average specific age of the methanogenic population.

Consequently, by suitably varying the operating conditions of the anaerobic reactors destined for the production of micro-organisms, a mixed biomass is obtained, which is suitable for producing cellular sensors with characteristics of amplified sensitivity to the toxic substances present in small concentrations, characterized by:

- a certain degree of cellular aggregation
- a high rate of cellular reproduction per single bacterial trophic group (young cells)
- a global metabolic chain not yet balanced in the methanogenic component (methanogens in multiplication).

The method, object of the present invention, for measuring the toxicity, involves the use of a series of anaerobic microreactors of 20–100 ml in volume, stirred, wherein supposedly toxic water or waste are tested (possibly with different dilutions). The measurement is effected on the basis of the different result which is registered under the same operating conditions of fermentation (pH, temperature, stirring, quantity of anaerobic biomass etc.) compared with one or more standard reference fermentations. The parameters on which the result is quantified with respect to the standard fermentation are the production of methane and biogas measured both in quantitative and kinetic terms.

As specified above, as a principle, one reactor is generally sufficient for each sample, but when greater precision is required, it may be convenient to use two or more reactors with different dilutions of water or water waste being tested.

Figure 1:
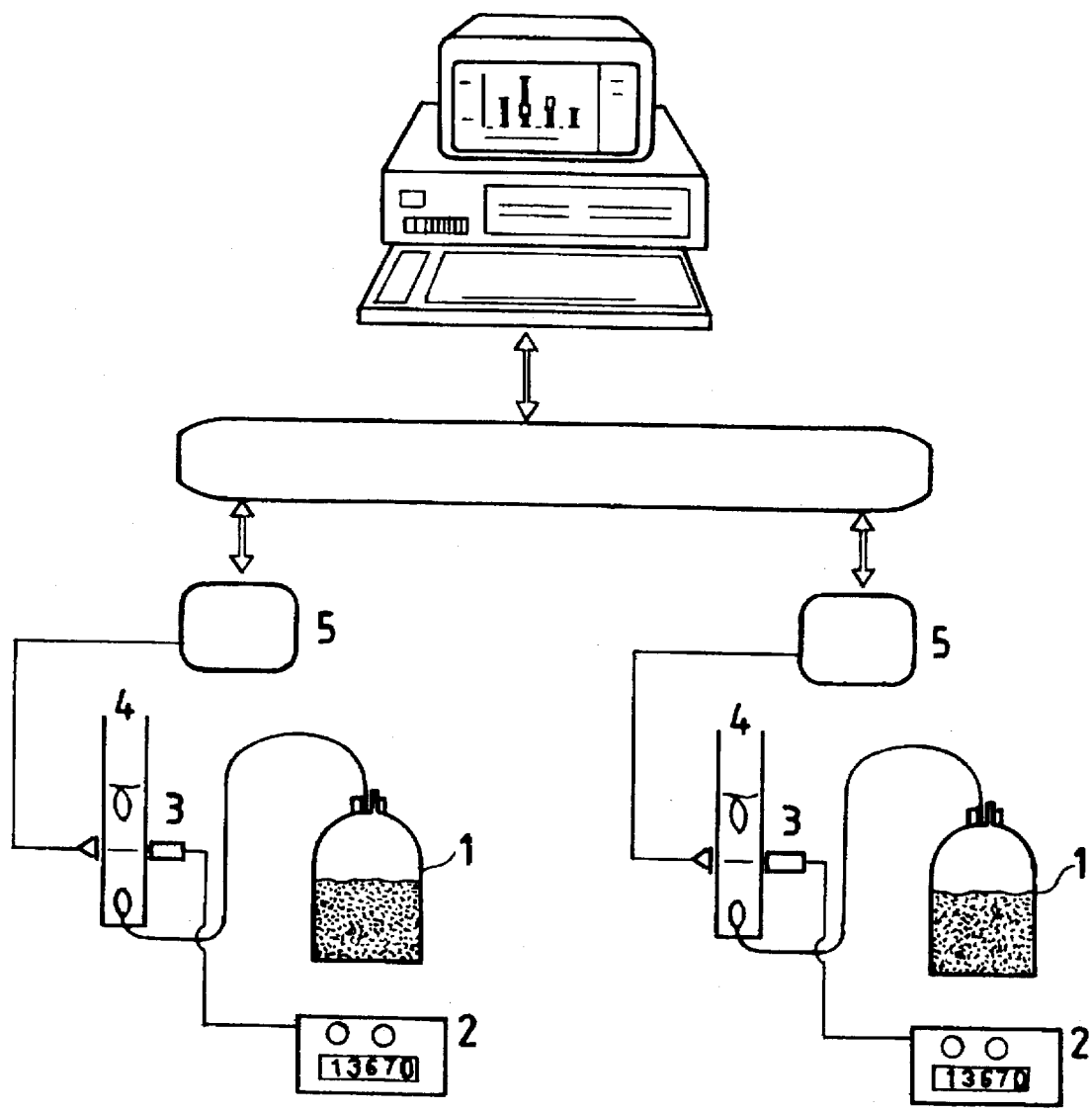
FIG. 1 illustrates the equipment used to perform the toxicity determination.

The microbic aggregates are used according to the procedure and equipment illustrated in a block diagram shown in FIG. 1.

A suitable substrate and an inoculum of anaerobic aggregate are placed in microreactors 1, which are at least two in number (one for the standard and the other for the water to be examined), in a quantity by weight of between 20 and 60 mg VSS (volatile suspended solids) corresponding to specific concentrations of between 1 and 3 g VSS/l. The microreactors are stirred at 200 rpm and thermostat-regulated at 35° C.

At the outlet of the microreactors are water seal cylinders 4 on which an optical system 3 is inserted, which for example can be a photodiode 2, suitably fed. The water seals are the same for each reactor both with respect to the dimensions of the cylinder and height of the liquid and to the length and diameter of the capillary from which the biogas (methane) is discharged.

The optical system counts the bubbles of biogas emitted from each microreactor and sends the relative signals to a memory 5. The memory is connected to a personal computer for the mathematical processing of the inhibition kinetics of the metabolic activity on the substrate present in the single reactor.

The values taken for a given sample are compared to the corresponding values of a reference standard and both the inhibition percentage (bacteriostasis) and total and irreversible inhibition (bactericide effect) are established of a given toxic substance acting in certain concentrations.

The duration of the test is about 3–6 hours. The procedure and equipment described can be "robotized" by automating the test procedure and the samples to be analyzed can be injected into the reactors with an automatic collection system of the commercial samples.

The method described can be applied not only to water destined for drinking and surface and ground water but also to effluents and industrial waste.

The sensitivity of the test is in the order of ppm.

In a further embodiment of the present invention the signals of the optical detecting system are sent by wire or radio to a remote signal processing system. In this way the analytical monitoring system described above can function as an alarm signal in the case of accidental toxicity or sudden variations in the standard characteristics of a given waste.

The examples which follow provide a better understanding of the present invention but do not limit it in any way.

EXAMPLE 1

Methanogenic anaerobic aggregates of the type commonly used for the purification of urban waste were used. The fermentations were carried out in bench-scale reactors with UASB configuration inoculated with 2.5 g VSS biomass per litre and maintained at a constant temperature of 35° C. The feeding substrate was composed of a solution of whey (5 g of whey in powder form per litre) to which inorganic salts such as $NH_4HCO_3$, $(NH_4)_2SO_4$, $CaCl_2$, $MgCl_2$, $FeCl_3$, $KH_2PO_4$, $K_2HPO_4$ had been added, with a final COD of 5000 ppm $O_2$ and a final $p_H$ of 6.8–7.2.

The characteristics of the mixed anaerobic bacterial aggregate obtained in a total of 25 days, feeding the fermenters in continuous with three cycles of decreasing HRT (Hydraulic Retention Time) (1.2; 1; and 0.85 days) are indicated below:

pH 6.8
Tot. suspended solids: 24.1 g/l
Volatile suspended solids (VSS) 8.8 g/l
Sedimentation rate: 29 m/h
COD (soluble) 256 ppm
Growth rate ($\mu$): 0.05 $h^{-1}$
Specific activity: 0.25 g $CH_4$/g VSS/d equal to 7.72 $\mu$mol $CH_4$/g VSS/min The biomass thus obtained was used to inoculate, in a quantity by weight of 58 g of VSS, four microreactors (each of 35 ml of which 20 ml operating volume) composed of Wheaton bottles for serology with a rubber top and metallic ring to keep in the gases and equipped with magnetic stirrers. The organic substrate of the four reactors was whey in powder form in a quantity of 50 mg per reactor. Trichlorophenol (2,4,6 trichlorophenol—TClF) was charged into three of the four reactors at a concentration of 50, 5 and 1 ppm respectively. The fourth reactor, under the same conditions and with the same substrate but without TClF, was kept as a control. The total duration of the test was 3 hours at a temperature of 35° C. and a stirring rate of 200 rpm.

Table 1 (where 0 indicates the standard and 1, 2, 3, the three dilutions of TClF) schematically shows the toxicity test of TClF measured as a reduction of the production kinetics of the biogas generated by the anaerobic metabolism.

TABLE 1

|  | 0 | 1 | 2 | 3 |
| --- | --- | --- | --- | --- |
| biomass mg VSS | 58 | 58 | 58 | 58 |
| TClF ppm | / | 50 | 5 | 1 |
| whey mg | 50 | 50 | 50 | 50 |
| $H_2O$ (up to ml) | 20 | 20 | 20 | 20 |

The head spaces of the microreactors were connected with water seals in a special support equipped with an optical sensor, in this specific case a photoelectric cell with a suitably fed photodiode. In this way at each passage of a bubble of biogas in the water seal an electrical signal was activated.

The events are totalized for each microreactor and suitably processed by connection with a PC. The mathematical statistical processing (using the program "Four" Borland Int.

nc. Scotts Valley Calif. USA) was carried out by linear regression of the approximately straight line of the kinetic curves of the frequency of events.

In the case of differential kinetics between sample and standard, the toxicity could be significantly expressed as a percentage of minor inclination of the processed line of the first with respect to the slope assumed by the second. The quantitative value was obtained by the complement to 100 of the ratio between the angular coefficients of the standard line and that of the line relating to the measurement reactors.

Figure 2:
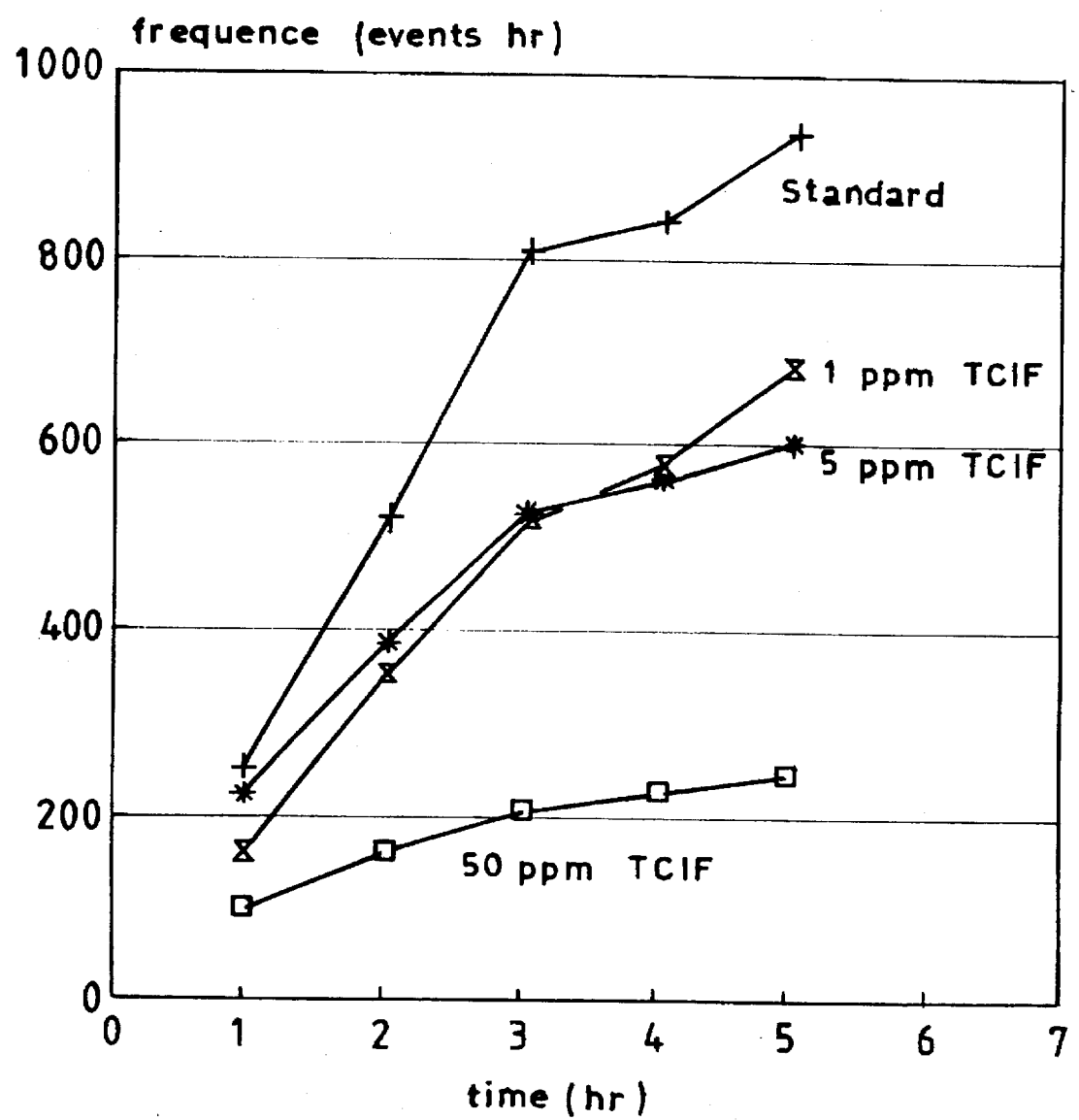
FIG. 2 is a graphical representation of the results of Example 1.

The results concerning the TClF are graphically shown in FIG. 2 and, as elaborated during 3 hours, in table 2.

It can be noted how the sensitivity to the toxic substance being tested on the part of the anaerobic aggregate can be significantly evaluated down to concentrations of 1 ppm (EC 37) and how with 5 ppm of TClF there is a toxicity of 46% (EC 46) with respect to the standard.

EXAMPLE 2

The same procedure and apparatus described in example 1 were used to evaluate the toxicity exerted by bivalent cations of metals such as Co and Zn.

The differences were as follows.

Figure 3:
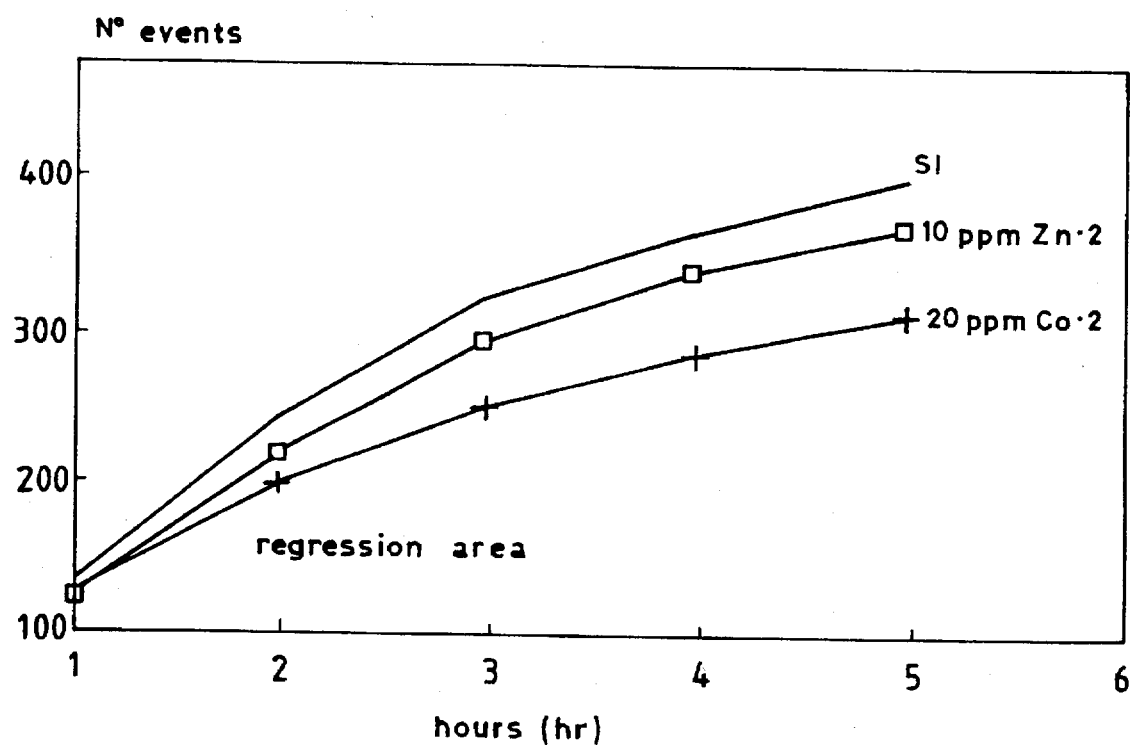
FIG. 3 is a graphical representation of the results of Example 2.

Concentrations of anaerobic aggregates of 43.8 mg per reactor; concentrations of Co and Zn ions of 20 and 10 ppm respectively; duration of the test 3 hours. FIG. 3 and table 3 show the results obtained. The toxicity exerted on the biomass by 20 ppm of Co ion and 10 ppm of Zn ion are 34% and 9% respectively.

EXAMPLE 3

The toxicity of 20 mg of tetrachloroethylene ($C_2Cl_4$) was tested using the same equipment and conditions as example 1.

In this case 20 mg VSS per reactor of anaerobic aggregates were used, characterized by a methanogenic activity of 0.11 g $CH_4$-COD per g VSS per day. As can be seen from table 4 there is a toxicity of 17.4% (EC 17) per 20 ppm of tetrachloroethylene.

TABLE 2

Toxicity of 2,4,6-Trichlorophenol (TClP)

| | (N° events/h) | | | |
|---|---|---|---|---|
| I test with photodiode h | Stand. | TClP 50 ppm | TClP 5 ppm | TClP 1 ppm |
| 1 | 251 | 97 | 224 | 159 |
| 2 | 520 | 160 | 386 | 353 |
| 3 | 810 | 204 | 524 | 515 |
| 4 | 848 | 224 | 560 | 576 |
| 5 | 938 | 242 | 599 | 682 |

Regr. over 3 hrs (I–III)

| | Standard | TClP 50 ppm | TClP 5 ppm | TClP 1 ppm |
|---|---|---|---|---|
| Constant | −32 | 46.66667 | 78 | −13.6667 |
| Stand. error of Y extimat. | 8.573214 | 7.756718 | 9.797959 | 13.06395 |
| Square R | 0.99953 | 0.989599 | 0.997871 | 0.997314 |
| N° of observat. | 3 | 3 | 3 | 3 |
| Degrees of freedom | 1 | 1 | 1 | 1 |
| Coefficient(s) X | 279.5 | 58.5 | 150 | 178 |
| Stand. error of Coeff. | 6.062178 | 5.484828 | 6.928203 | 9.237604 |
| Tox (%) | — | 80.8 | 46.3 | 37.2 |

TABLE 3

Toxicity of Co++ (CoCl2) and of Zn++ (ZnSO4.7H2O) Byomass Typ. 2; Colture IV

| | N° of bubbles (Photodiode - photodetector) | | |
|---|---|---|---|
| h | Stand. (2) | Co++ 20 ppm | Zn++ 10 ppm |
| 1 | 131 | 126 | 121 |
| 2 | 242 | 199 | 219 |
| 3 | 323 | 252 | 296 |
| 4 | 365 | 288 | 340 |
| 5 | 400 | 314 | 369 |

Regr. over 3 hrs (I–III)

| | Stand. (2) | Co++ 20 ppm | Zn++ 10 ppm |
|---|---|---|---|
| Constant | 40 | 66.33333 | 37 |
| Stand. error of Y extimat. | 12.24745 | 8.164966 | 8.573214 |
| Square R | 0.991928 | 0.991672 | 0.995223 |
| N° of observations | 3 | 3 | 3 |
| Degrees of freedom | 1 | 1 | 1 |
| Coefficient(s) X | 96 | 63 | 87.5 |
| Stand. error of Coeff. | 8.660254 | 5.773503 | 6.062178 |
| Tox (%) | — | 34.4 | 8.9 |

TABLE 4

Toxicity of C2Cl4 20 ppm Byomass V Colture cons. at 3° C. of 13.05.93

| | N° of bubbles/hr (Photodiode - photodetector) | |
|---|---|---|
| | 20 mg VSS | |
| h | Standard | C2Cl4 |
| 1 | 52 | 49 |
| 2 | 92 | 86 |
| 3 | 178 | 149 |
| 4 | 296 | 277 |
| 5 | 339 | 342 |

Regr. over 3 hrs (I–III)

| | 20 mg VSS | |
|---|---|---|
| | Standard | C2Cl4 |
| Constant | −15.3333 | −5.33333 |
| Stand. error of Y extimat. | 16.73818 | 10.61446 |
| Square R | 0.963139 | 0.977963 |
| N° of observations | 3 | 3 |
| Degrees of freedom | 1 | 1 |
| Coefficient(s) X | 60.5 | 50 |
| Stand. error or Coeff. | 11.83568 | 7.505553 |
| Tox (%) | — | 17.4 |

We claim:

1. A method for determining the toxicity of water and water discharges, comprising the following steps:

(a) preparing a mixed methanogenic anaerobic bacterial culture by incubating a methanogenic anaerobic aggregate in a feeding substrate comprising whey;

(b) inoculating the bacterial culture in a plurality of reactors of which at least one is a reference reactor, containing a substrate with standard water and at least another, a measurement reactor, containing the substrate with water or waste the toxicity of which is to be measured;

said measurement and reference reactors being connected to a detecting system capable of measuring the volume of biogas produced per unit of time;

said detecting system being operatively connected to a data processing system capable of determining the decrease in the production kinetics of the biogas generated by the anaerobic metabolism on the substrate and capable of correlating it with toxicity of the water or waste;

(c) measuring the volume of biogas produced per unit time in the measurement and reference reactors; and (d) correlating a lower level of production of biogas in the measurement reactor in comparison to the reference reactor with toxicity of the water or waste in the measurement reactor.

2. The method according to claim 1, wherein the biogas produced is methane.

3. The method according to claim 1, wherein the detecting system is a photodiode.

4. The method according to claim 1, wherein the reactors are one reference reactor and two measuring reactors with different concentrations of water or waste the toxicity of which is to be measured.

* * * * *